United States Patent [19]

Holt et al.

[11] Patent Number: 5,062,840
[45] Date of Patent: Nov. 5, 1991

[54] DISPOSABLE DIAPERS

[76] Inventors: John N. Holt; Debra S. Holt, both of Box 4, Ralston, Okla. 74650

[21] Appl. No.: 355,654

[22] Filed: May 22, 1989

[51] Int. Cl.[5] .............................................. A41B 13/02
[52] U.S. Cl. .................................................. 604/385.1
[58] Field of Search ..................... 604/385.1, 386, 387, 604/388, 389, 390, 391, 392, 393

[56] References Cited

U.S. PATENT DOCUMENTS

| | | | |
|---|---|---|---|
| 2,154,332 | 4/1939 | Hirsch | 604/385.1 |
| 2,532,029 | 11/1950 | Medoff | 604/394 |
| 3,192,926 | 7/1965 | Callaghan | 128/286 |
| 3,322,122 | 5/1967 | Daniel | 128/284 |
| 3,356,091 | 12/1967 | Patterson | 128/286 |
| 3,530,859 | 9/1970 | Helmowitz | 128/284 |
| 3,776,233 | 12/1973 | Schaar | 604/385.1 |
| 3,874,385 | 4/1975 | Gellert | 128/287 |
| 3,890,973 | 6/1975 | Davis et al. | 604/392 |
| 4,027,672 | 6/1977 | Karami | 604/385.1 |
| 4,200,102 | 4/1980 | Duhamel et al. | 128/286 |
| 4,501,586 | 2/1985 | Holtman | 604/385.1 |
| 4,560,380 | 12/1985 | Tharel | 604/385 |
| 4,576,596 | 3/1986 | Jackson et al. | 604/385.1 |
| 4,616,785 | 6/1987 | Battista | 604/385.1 |
| 4,662,877 | 5/1987 | Williams | 604/385 |
| 4,678,464 | 7/1987 | Holtman | 604/385.1 |
| 4,685,916 | 8/1987 | Enloe | 604/385 |
| 4,778,459 | 10/1988 | Fuisz | 604/385.1 |

*Primary Examiner*—David J. Isabella
*Attorney, Agent, or Firm*—Head & Johnson

[57] ABSTRACT

An improved diaper to allow fecal materials both solid and semi-solid to be retained away from the body. It includes a water impervious outer layer, a water retention or absorption intermediate layer and an inner or inside layer which is water pervious. The inner layer has an anal opening for waste passage. Immediately below the anal opening in the intermediate layer is an oval shaped solids cavity. Solid waste material from the baby will be deposited in this cavity and may extend in the space between the intermediate layer and the outer layer. The outer layer has a pleat which is aligned with the solids cavity to give more room for waste products. A water soluble cover, which disintegrates in water, may be provided for the solids cavity of the intermediate layer.

13 Claims, 9 Drawing Sheets

DISPOSABLE DIAPERS

BACKGROUND OF THE INVENTION

1. Field of the Invention:

This invention relates generally to diapers for the containment of body waste and particularly on infants.

2. Background:

Disposable diapers have been used rather widely over the last thirty to forty years and, in fact, constitute a major industry. Typically, the disposable diapers comprise a liquid impermeable plastic backing or outer sheet, an intermediate layer which may be a wood pulp absorbent bat, and a moisture permeable inner or facing sheet which would be against the infant. The components are generally secured together by lines of adhesive with the backing and facing sheets usually directly adhesively interconnected around peripheral portions of the diaper. Some disposable diapers include elastic bands for providing the shaping and/or gathering effect for the diaper in the crotch region and facilitating the establishment of a fluid resistant seal around the infants legs.

A great deal has been accomplished in the field of the disposable waste collecting garments used on children. Their increased ability to remove liquids away from the body and increase capacity to store liquids has helped them to almost completely replace the older cloth garments. But, most of the improvements in such garments have been directed in the ability to handle liquid waste. In actual practice, however, the use to which such garments are subjected is that they are called upon not only to retain liquid but on a daily basis they are called upon to retain both solids and semi-solids excreted from the digestive track. For the most part the way the garments have been improved to deal with such waste has been by improving the ability of the leg and waste openings to minimize leakage to outer garments. This is necessary because such garments are ill prepared to deal with such waste. As every mother knows the solution that merely stops the leakage is actually no solution at all. What happens many times when the child does not have a very firm bowel movement, the excretement is crushed and spread between the child's body and the inner permanent layer of the diaper. Such spreading of waste on a child's body contributes to constant filth and its associated rashes, skin irritations and untold discomfort caused by such unsanitary conditions.

It is therefore seen that there is a definite and urgent need for a diaper which can contain the solid waste material and keep it from being spread over a substantial portion of the area covered by the diaper. It is therefore an object of this invention to provide an improved disposable diaper which will prevent the spreading and smearing of the child's solid waste.

SUMMARY OF THE INVENTION

This is a disposable garment such as a disposable diaper which is suited not only for liquid retention but also especially designed to allow fecal materials, both solid and semi-solid, to be retained away from the child's body thus allowing the child's body to stay cleaner, dryer and greatly aid in the elimination of rashes and skin irritations which are so common with present disposable waste retention garments. In a preferred embodiment this includes a three-layer diaper which has a water impervious outer or backing layer, a water retention or absorption intermediate layer and an inner or inside layer made of water pervious or permeable material. These layers are greatly modified from the existing disposable diapers. The inner layer has an anal opening for waste passage which is properly positioned on the inner layer to receive anal solid discharge when placed on a child. The intermediate layer is provided with a oblong cavity which is preferably cut all the way through the intermediate layer. A water soluble cover which may be simply a piece of paper tissue, is placed over the oblong cavity. Preferably, the outer or backing layer is provided with a pleat which extends along underneath the oblong cavity.

This improved diaper is placed on the child and held thereon in the usual manner by fastening tapes and so forth. When the child has a bowel movement the solid waste passes through the anal opening of the inside layer, through the solids cavity of the intermediate layer and into the cavity or valley which is formed when the pleat in the outer layer is expanded. This keeps the solid wastes in the confined space. In one embodiment a water soluble cover is provided for the oblong cavity in the intermediate layer. This is primarily to improve the looks. In another embodiment, the outer layer does not have a pleat but the intermediate layer has a large slit area. In still another embodiment the intermediate layer is provided with valleys or grooves or depressed areas near the anal opening of the inside layer to provide volume for receiving the solid waste material.

As will be seen with the detailed description, there is provided hidden recesses or cavities not found in prior diapers but are in our diaper and provides sanitary storage of the child's solid waste.

DESCRIPTION OF THE PREFERRED EMBODIMENT

Figure 1:
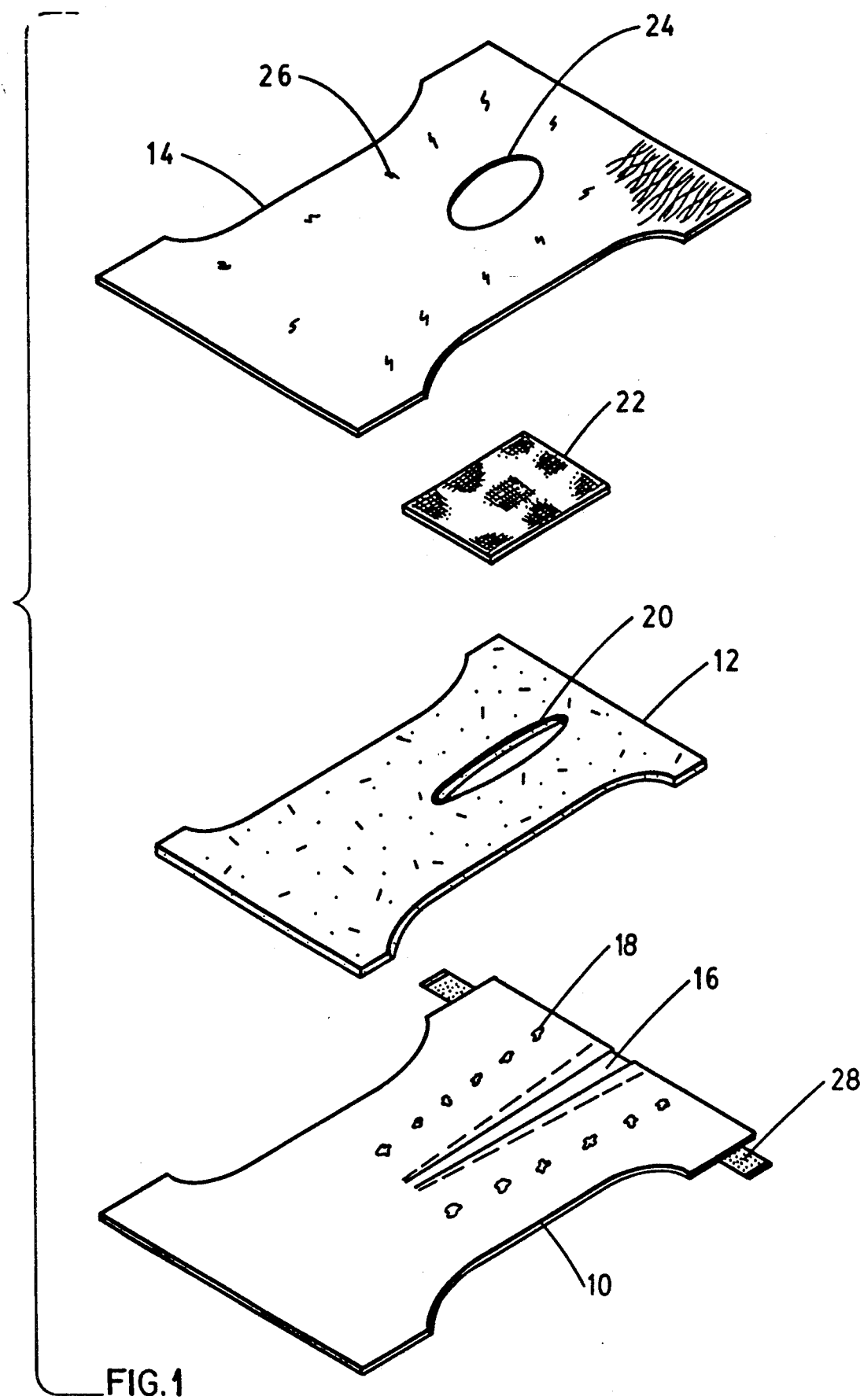
FIG. 1 shows in exploded view the three layers of our diaper.

Attention is next directed to FIG. 1 which shows our improved disposable diaper in exploded form. There are three main layers. Shown thereon is water impervious outer layer 10, a water retention or absorbent intermediate layer 12, and an inner or inside layer 14. The outer layer 10 has pleat 16 which is in the back rear panel to allow for expansion to form a receiving space for solid waste. The pleat is more clearly shown in FIGS. 2 and 3. Glue deposits 18 are deposited along either side of the pleat 16 to hold the intermediate layer 12 in place when it is positioned on top of the outer layer 10. The intermediate layer 12 is a water retention layer and may be made of any of the various water retention materials presently used in commercially available diapers. One suitable material could be refined wood pulp. The intermediate layer has a solids cavity opening 20 which is positioned on the layer such that it will surround the rectum of the baby when the diaper is placed thereon. A water destructive cover 22 may be placed on cavity 20 of the intermediate layer 12 such as indicated more clearly in FIG. 5.

Figure 6:
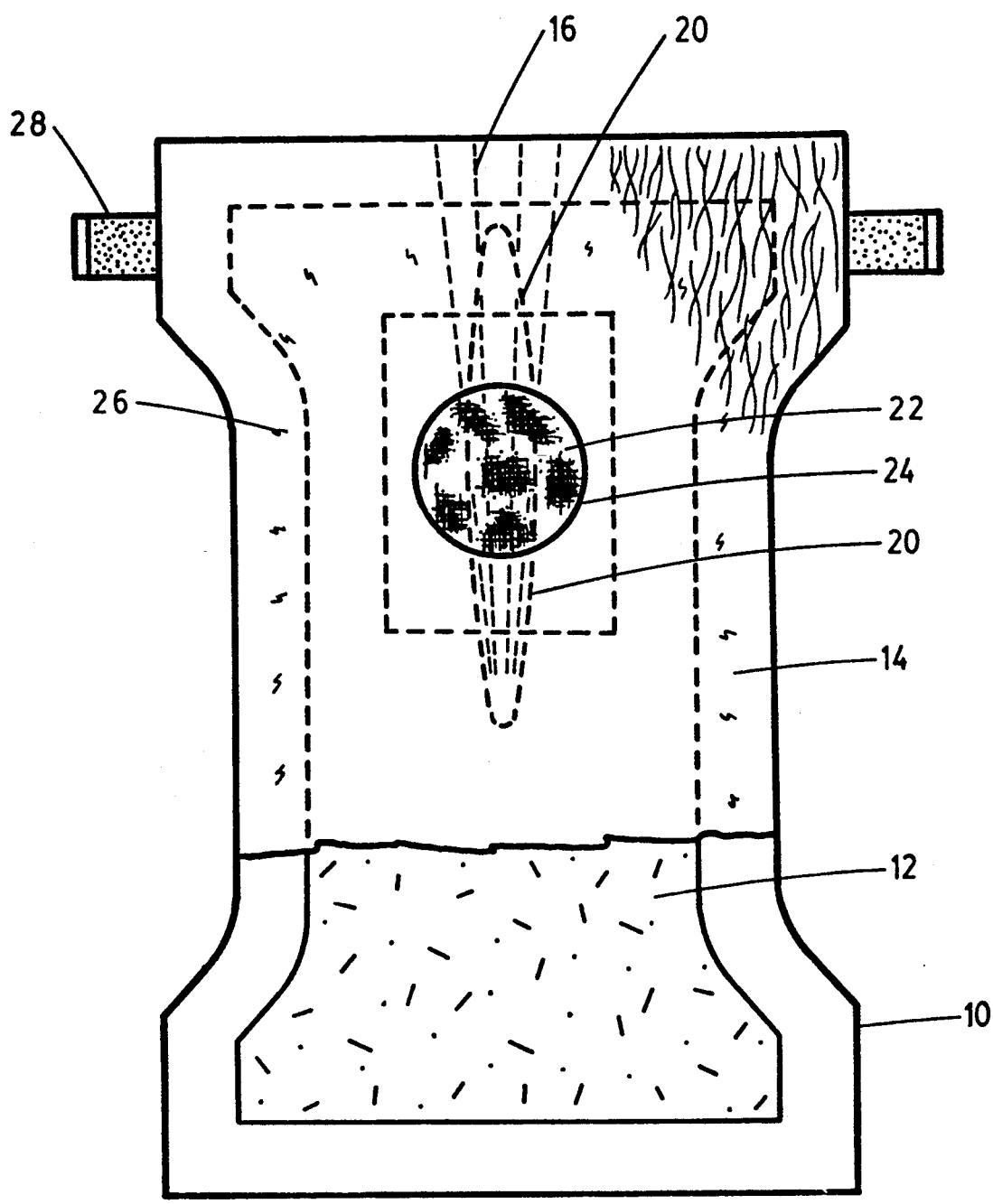
FIG. 6 is a plan view with all three layers assembled together with a part of the inside layer removed.

The inner layer 14 has anal opening 24 which as shown in FIG. 6 fits over the solids cavity 20 of intermediate layer 12 when the diaper is assembled. The inner layer 14 is of a material to be comfortable next to the baby's body and it must be water permeable so that water can easily pass through and the material should remain dry to the touch. Elasticity means 26 are provided on the inner layer to give better fit than is presently done on disposable diapers.

Figure 2:
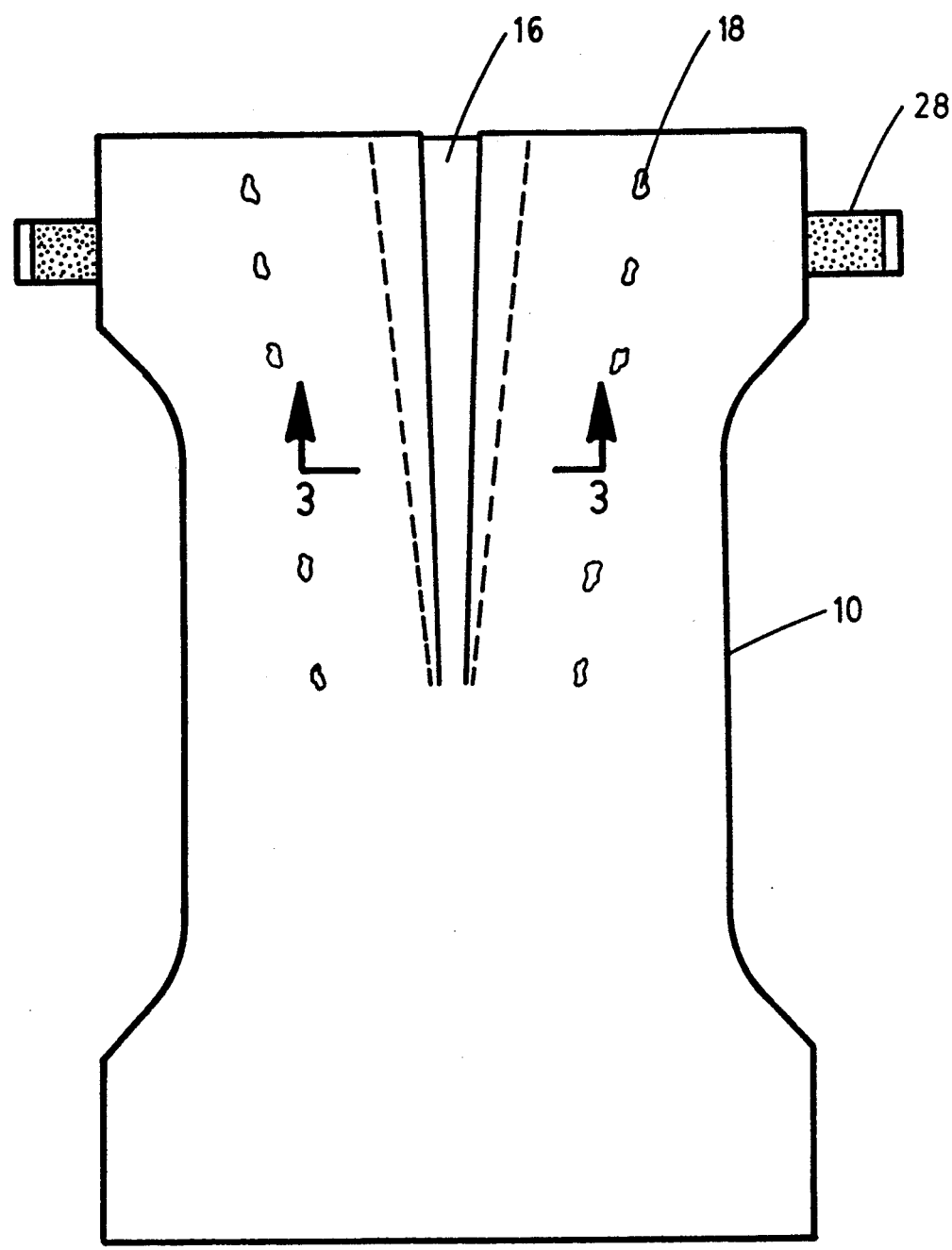
FIG. 2 is an enlarged view of the backing or outer layer.
Figure 3:
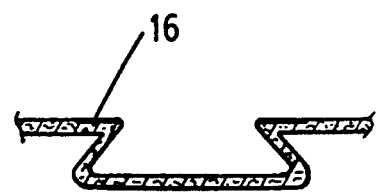
FIG. 3 is a view taken along the line 3—3 of FIG. 2.
Figure 4:
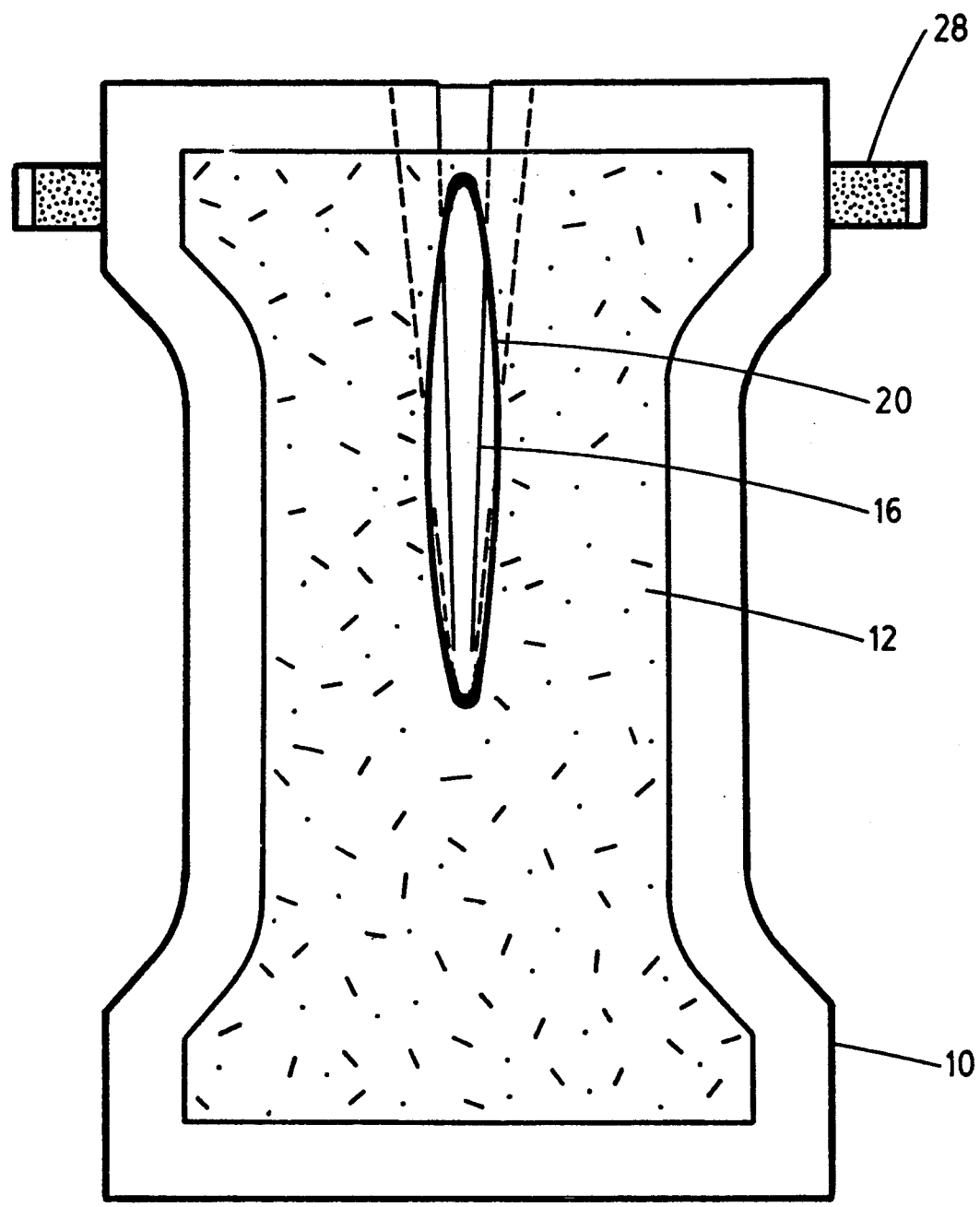
FIG. 4 is a plan view of the intermediate layer placed on top of the backing or outer layer.

The assembly of the layers shown in FIG. 1 into a completed diaper is rather straight forward. As shown in FIG. 2 the outer layer 10 has a pleat 16 and globs of glue 18. Fastening tabs 28 are also provided as in a conventional diaper. FIG. 4 shows the intermediate layer 12 secured to the outer layer 10 and is conveniently secured thereto by the glue spots 18. As can be seen, the solids cavity 20 is positioned directly over the completed section 16.

Figure 5:
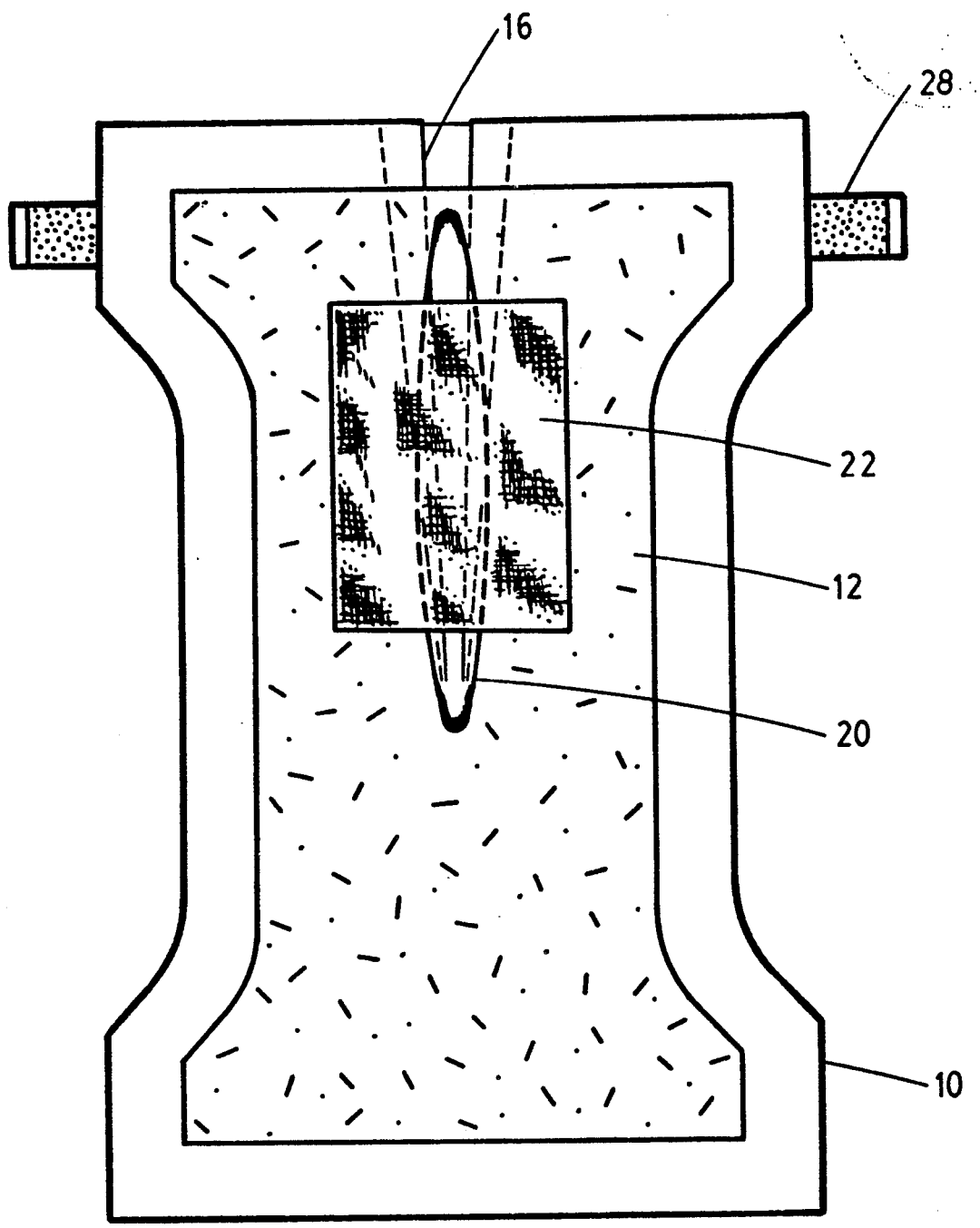
FIG. 5 is similar to FIG. 4 except that a water moisture destructive cover is shown over the oblong opening in the intermediate layer.

Attention is next directed to FIG. 5 which is the same as FIG. 4 except that water destructible cover 22 has been loosely positioned over cavity 20 between the inner layer and the intermediate layer 12 to allow for easy movement. This cover 22 is moisture destructive and although not absolutely necessary to the operation of the garment may serve three purposes. It gives the garment or the diaper a finished appearance and will enfold firm waste and enclose them in the closed layers of the garment. If the movement is soft the layer will disintegrate and allow all material to pass through into the space within or between the lower layers and thus away from the body.

FIG. 6 shows the assembled diaper in plan view with a portion of the inner layer 14 cut away. The outer layer 10 is on bottom with the intermediate layer 12 glued thereon as indicated in FIG. 5. The inner layer 14 is secured to the outer layer along the overlap of the intermediate layer 12. The positioning of the pleat 16 in the outer layer, the solids cavity 20 in the intermediate layer and the anal opening 24 in the inner layer are shown in position. Also shown, although not absolutely essential is the water soluble cover 22. Reference number 26 indicates additional elasticity in the inner layer of the garment over what is normally done. This permits a snug fit of the layer which helps the diaper to work effectively. From the assembled drawing it is seen that the pleat 16 in the water impervious outer layer 10 preferably runs from the area of the waist band into the crotch area between the legs. These additional folds allow the outer layer of the garment to expand to larger overall dimensions than the inner layers thus allowing for additional available space when needed between the outer layer and the other layers to form a storage space for the solid discharge waste from the baby. In service the waste passes from the baby through the anal opening 24 into the solids cavity 20 which lets excess waste enter into the pleated space 16 as just indicated. This opening or slit 20 allows the feces from the digestive track to move through this layer of the garment and thus away from the body into the aforementioned area that is now available next to the outer layer of the garment as in the pleated area 16.

The modifications of the inner layer, intermediate layer and the outer layer of the anal opening 24, solids cavity 20 and the pleats 16 allow any waste material whether solid, semi-solid or even liquids from the digestive track to have room to move away from the body and into the outer areas between the layers of the garments thereby greatly reducing the amount of waste which is held in close proximity to the body.

Figure 7:
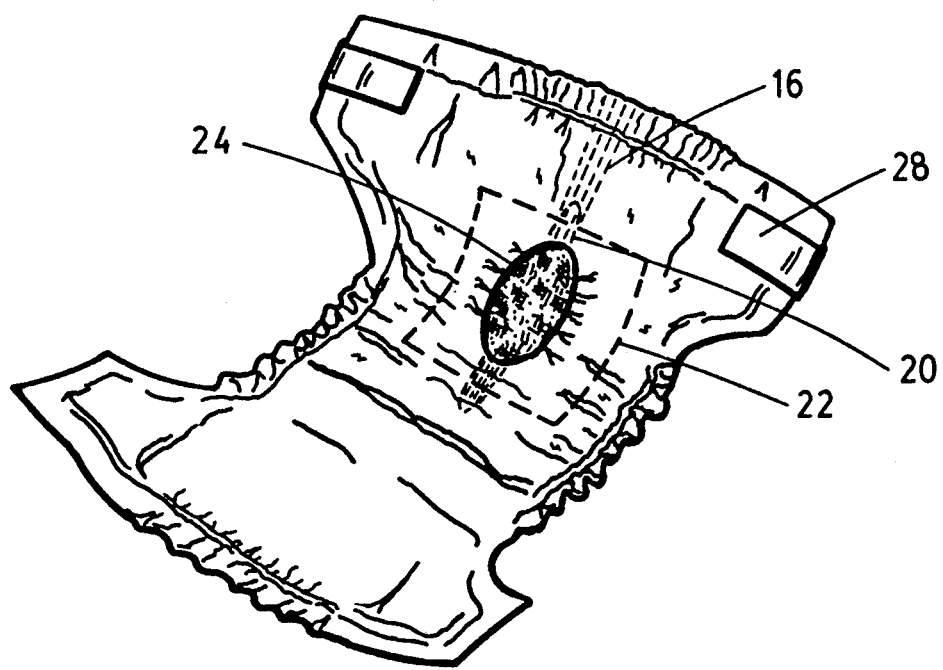
FIG. 7 is an isometric view shown the completed diaper.

FIG. 7 shows an isometric view of the diaper in its finished form.

Figure 8:
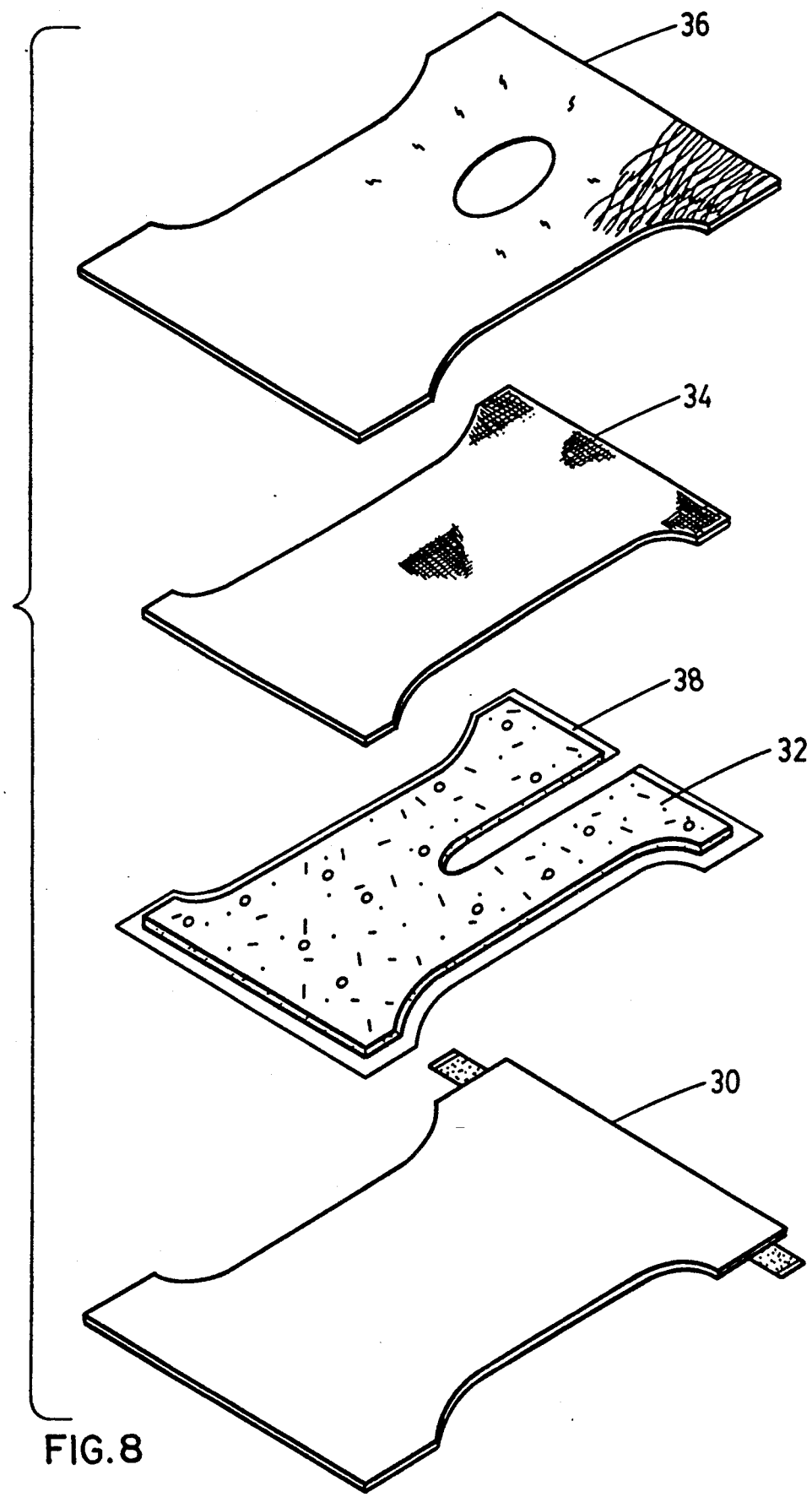
FIG. 8 is an exploded view showing a different embodiment of the invention.

Attention is next directed to FIG. 8 which shows another embodiment of this invention. Shown thereon is outer layer 30 intermediate layer 32, cover 34 and inner layer 36. These may be made of the same material respectively as the outer layer 10, intermediate layer 12, cover 22 and inside layer 14 shown in FIG. 1. In this embodiment it is preferred that the various layers 32, 34, 36 all be the same size. The main differences are that outer layer 30 has no pleat, the intermediate layer 32 has a long slit 38 instead of the smaller anal cavity 20 of FIG. 1. The cover 34 is the same size as the other layers. The inner layer 36 is substantially identical to layer 26 of FIG. 1. Instead of glue holding the layers together the water impervious outer layer 30 may be sewn at the outer extremities to a film or edging 38 which is attached to the outer extremities of the intermediate layer 32. Inasmuch as the moisture absorbent material of intermediate layer 32 is not glued to the outer layer 30 any needed space to retain or store the solid waste material can be had by expansion between the intermediate layer 32 and the outer layer 30.

Figure 9:
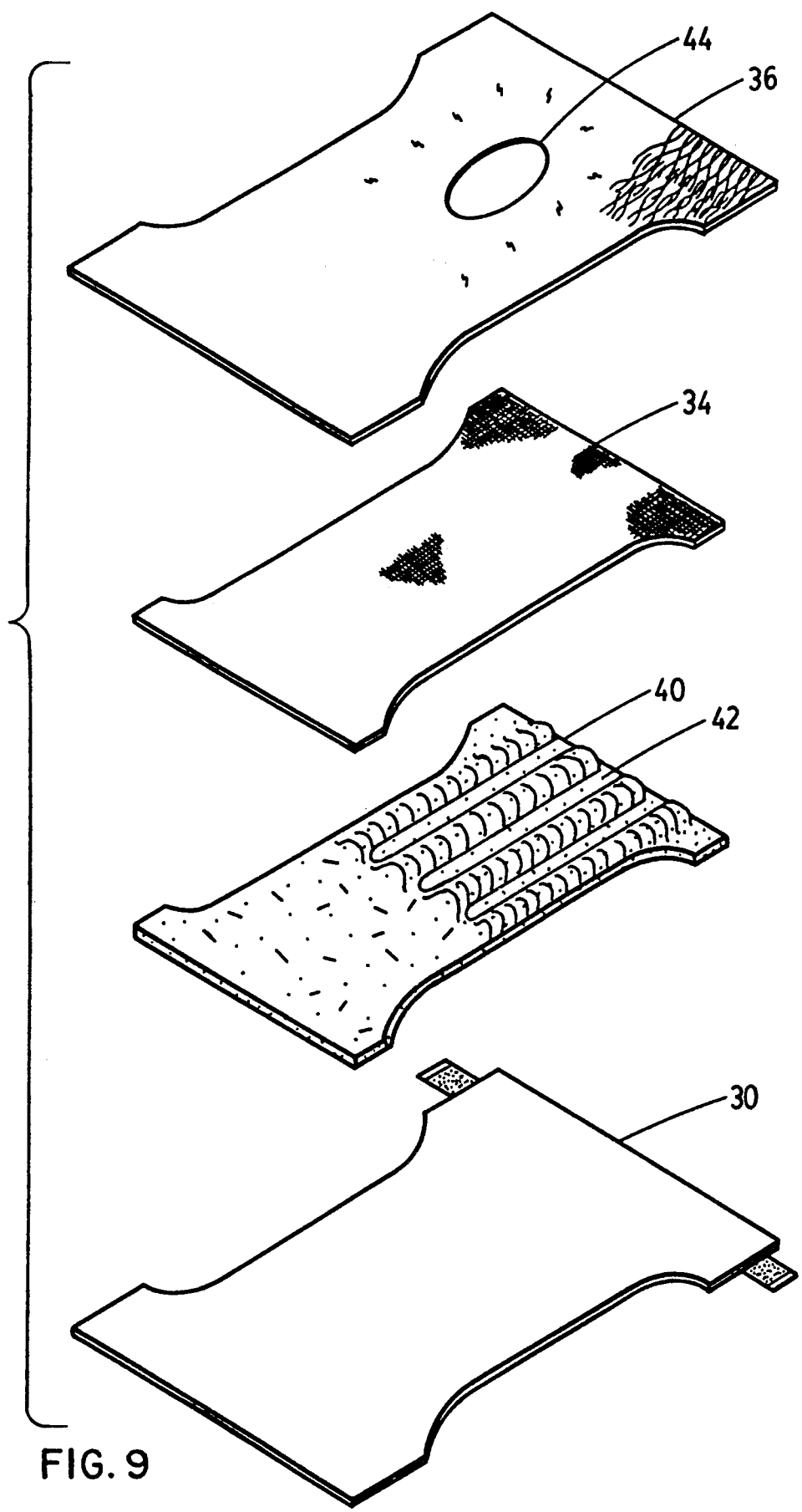
FIG. 9 is an exploded view showing the three layers with a cover sheet between the intermediate layer and the inside layer and illustrates still another embodiment.

Attention is next directed to FIG. 9 which shows a still further embodiment of our invention. This embodiment is quite similar to that of FIG. 8 except that the intermediate layer of FIG. 9 is different from intermediate layer 32 of FIG. 8. This is adapted to reception and retention of solid waste not by the open areas such as slot 38 of intermediate layer 32 of FIG. 8, but by surface irregularities creating grooves or valleys 42 or other indentation in the proximate area of the anal opening 44.

Figures 10, 11:
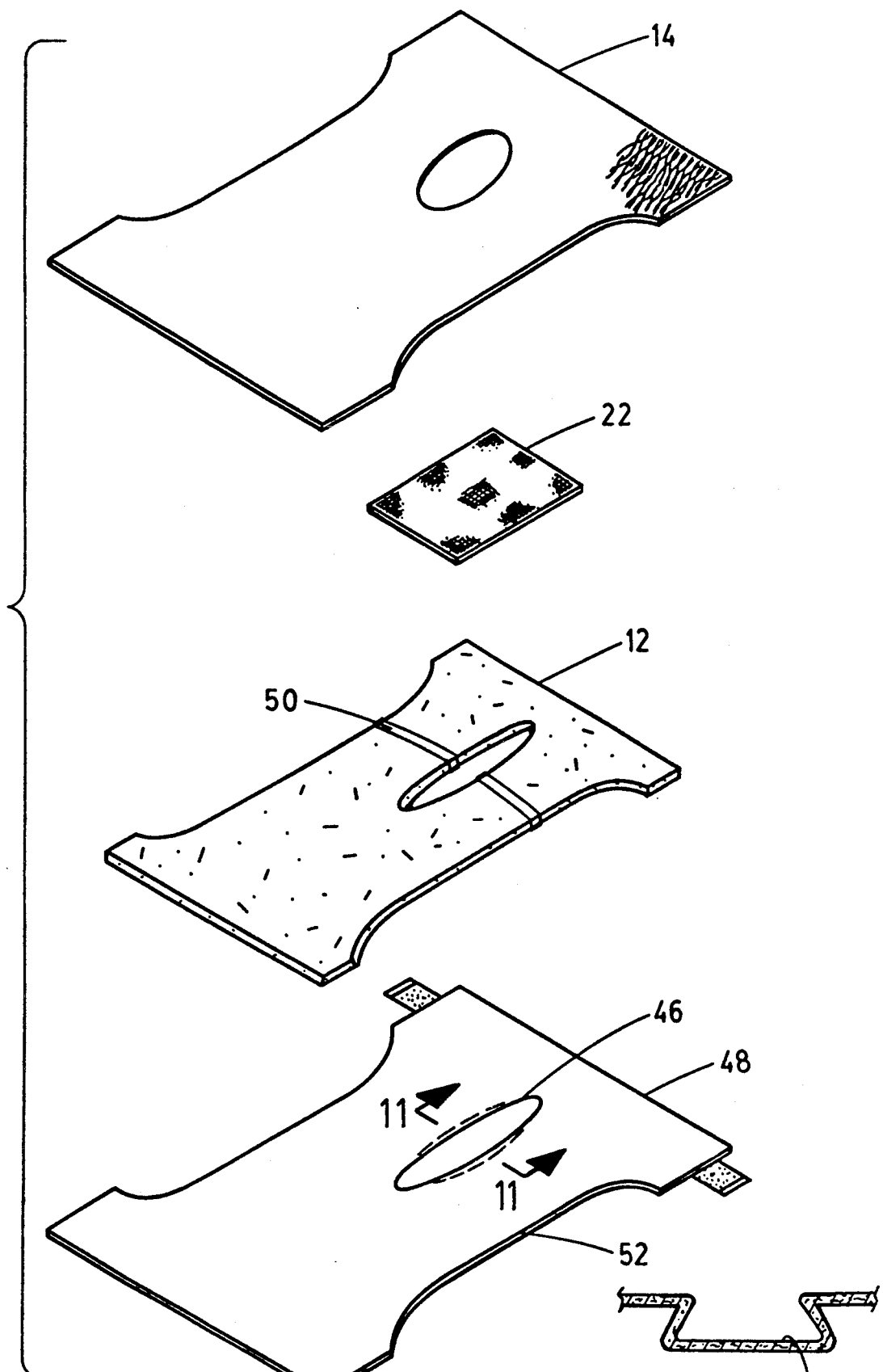
FIG. 10 is an exploded view similar to FIG. 1 that shows still another embodiment of the invention in which the outer or backing sheet has an oval shaped cavity.
FIG. 11 is a view taken along the line 11—11 of FIG. 10.

Attention is next directed to FIGS. 10 and 11 which show a still further embodiment of our invention. This embodiment is quite similar to those shown in FIG. 1 except that the outer layer has been modified. The intermediate layer 12, inner layer 14 and cover 22 are identical to those numbers of FIG. 1 except that a restraining tape or string or ribbon 50 has been added to keep the cavity open in layer 12. Outer layer 50 has an oval opening 46 which opens into a pleated area which pleated section in cross section is shown in FIG. 11. Here the pleats do not go to the waist 48, but are merely confined to the general area of the opening 46. In this embodiment, as well as the other embodiments, structure is provided whereby the solid waste from the baby will be passed through anal opening 44 into cavities or solid waste receiving space away from the baby's skin to greatly reduce the amount of waste which may be in proximity to the body. This allows the child's body to stay cleaner, dryer and greatly aids in the elimination of rashes and skin irritations which are so common with the prior disposable waste retention garments.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A disposable diaper comprising:
   a water permeable inner layer having an opening therein shaped to surround a wearer's anal opening;
   a water retention absorbent intermediate layer having a void positioned at least partially under said opening of said inner layer for receiving solid waste excretement from a wearer;
   a water impervious outer layer adjacent said intermediate layer;
   means to hold said inner layer, said intermediate layer and said outer layer in position.

2. A disposable diaper as defined in claim 1, said void comprising an opening through said intermediate layer.

3. A disposable diaper as defined in claim 1, said diaper having a waist portion and said void being cut from said waist portion across said opening in said inner layer.

4. A disposable diaper as defined in claim 1, said diaper having a waist portion and said outer layer having a pleat extending from said waist portion across said opening in said inner layer.

5. An apparatus as defined in claim 1 further comprising a cover sheet placed over at least a part of said void in said intermediate layer.

6. A disposable diaper as defined in claim 1, said void of said intermediate layer comprising depressed areas to receive the solid waste from the infant.

7. A disposable diaper as defined in claim 6 further comprising a cover sheet which disintegrates in water and is placed between said inner layer and said intermediate layer.

8. A disposable diaper as defined in claim 1, said void comprising an oblate opening in said intermediate layer whose extremities do not extend to any edge and a pleat means in said outer layer aligned with said oblate opening.

9. A disposable diaper for an infant having a receiving space for infant solid waste to be stored away from the body which comprises:
   an inner layer which is water pervious;
   an outer layer which is water impervious;
   an intermediate layer which has water retention capabilities;
   said inner layer having an opening shaped to surround a wearer's anal opening;
   said intermediate layer having a cavity which is positioned at least partially under said opening of said inner layer;
   said outer layer having a pleat which is positioned adjacent said cavity, said pleat forming a solids receiving cavity which opens under said cavity of said intermediate layer; and
   means to hold said inner layer, said intermediate layer and said outer layer in a secured position with respect to each other.

10. A disposable diaper as defined in claim 9 including a water disintegratible cover positioned under said opening in said inner layer between said inner layer and said intermediate layer.

11. A disposable diaper comprising:
    a water permeable inner layer having an opening therein shaped to surround a wearer's anal opening;
    a water retention absorbent intermediate layer having a void consisting of depressed areas to receive solid waste from an infant;
    a water impervious outer layer adjacent said intermediate layer;
    a cover sheet which disintegrates in water disposed between said inner layer and said intermediate layer and covering said opening in said inner layer; and
    means to hold said inner layer, said intermediate layer and said outer layer in position.

12. A disposable diaper for an infant having a receiving space for infant solid waste to be stored away from the body comprising:
    an inner layer which is water pervious;
    an outer layer which is water impervious;
    an intermediate layer which has water retention capabilities;
    said inner layer having an opening shaped to surround a wearer's anal opening;
    said intermediate layer having a cavity which is positioned at least partially under said opening of said inner layer;
    means to hold said inner layer, said intermediate layer and said outer layer in a secured position with respect to each other.

13. A disposable diaper comprising:
    a water permeable inner layer having an opening therein shaped to surround a wearer's anal opening;
    a water retention absorbent intermediate layer having an oblate void substantially longer and substantially narrower than said opening positioned at least partially under said opening of said inner layer for receiving solid waste excretement from a wearer;
    a water impervious outer layer adjacent said intermediate layer; and
    means to hold said inner layer, said intermediate layer and said outer layer in position.

* * * * *

REEXAMINATION CERTIFICATE (2449th)
United States Patent [19]
Holt et al.

[11] B1 5,062,840
[45] Certificate Issued Jan. 3, 1995

[54] DISPOSABLE DIAPERS

[76] Inventors: John N. Holt; Debra S. Holt, both of Box 4, Ralston, Okla. 74650

Reexamination Request:
No. 90/002,896, Nov. 19, 1992

Reexamination Certificate for:
Patent No.: 5,062,840
Issued: Nov. 5, 1991
Appl. No.: 355,654
Filed: May 22, 1989

[51] Int. Cl.$^6$ ............................................. A41B 13/02
[52] U.S. Cl. .................................................... 604/385.1
[58] Field of Search ............................. 604/355, 385.1

[56] References Cited
U.S. PATENT DOCUMENTS

| | | | |
|---|---|---|---|
| 2,043,325 | 6/1936 | Jackson, Jr. | 604/385.2 |
| 2,154,332 | 4/1939 | Hirsch | 604/385.1 |
| 3,890,973 | 6/1975 | Davis et al. | 604/385.1 |
| 4,731,065 | 3/1988 | Yamada | 604/355 |
| 4,834,737 | 5/1989 | Khan | 604/385.2 |

*Primary Examiner*—David J. Isabella

[57] ABSTRACT

An improved diaper to allow fecal materials both solid and semi-solid to be retained away from the body. It includes a water impervious outer layer, a water retention or absorption intermediate layer and an inner or inside layer which is water pervious. The inner layer has an anal opening for waste passage. Immediately below the anal opening in the intermediate layer is an oval shaped solids cavity. Solid waste material from the baby will be deposited in this cavity and may extend in the space between the intermediate layer and the outer layer. The outer layer has a pleat which is aligned with the solids cavity to give more room for waste products. A water soluble cover, which disintegrates in water, may be provided for the solids cavity of the intermediate layer.

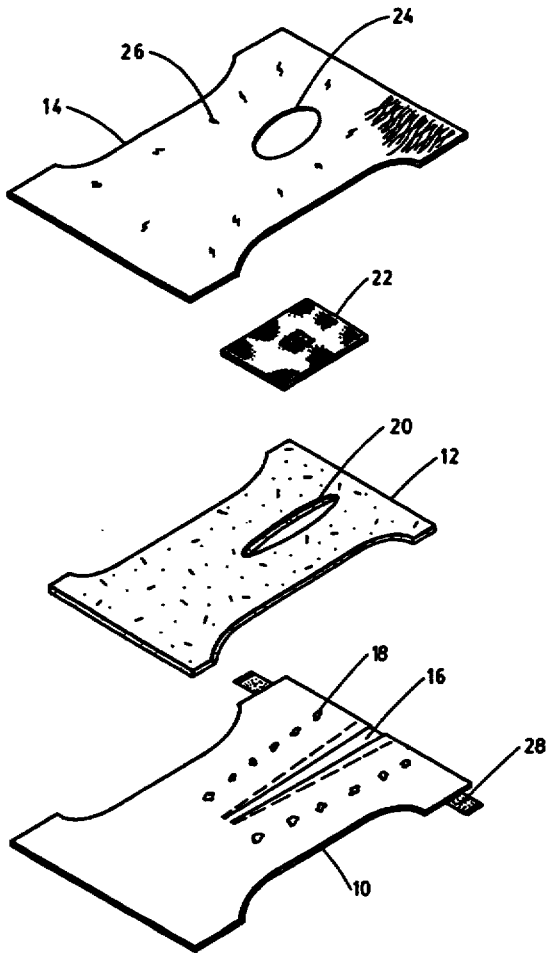

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 11 & 13 is confirmed.

Claims 1, 9 and 12 are determined to be patentable as amended.

Claims 2-8, and 10, dependent on an amended claim, are determined to be patentable.

New claims 14-23 are added and determined to be patentable.

1. A disposable diaper comprising:
   a water permeable inner layer having an opening therein shaped to surround a wearer's anal opening;
   a water retention absorbent intermediate [layer having a void positioned at least partially under said opening of said inner layer for receiving solid waste excretement from a wearer] *layer, said intermediate layer having a cavity, larger than said opening, and positioned under said opening of said inner layer to entrap waste and preventing the waste from being spread over a substantial portion of a diaper;*
   a water impervious outer layer adjacent said intermediate layer;
   means to hold said inner layer, said intermediate layer and said outer layer in position.

9. A disposable diaper for an infant having a receiving space for infant solid waste to be stored away from the body which comprises:
   an inner layer which is water pervious;
   an outer layer which is water impervious;
   an intermediate layer which has water retention capabilities:
   said [inner] *intermediate* layer having an opening shaped to surround a wearer's anal opening;
   said intermediate layer having a [cavity which is positioned at least partially under said opening of said inner layer] *cavity, larger than said opening, and positioned under said opening of said inner layer to entrap waste and preventing the waste from being spread over a substantial portion of a diaper;*
   said outer layer having a pleat which is positioned adjacent said cavity, said pleat forming a solids receiving cavity which opens under said cavity of said intermediate layer; and
   means to hold said inner layer, said intermediate layer and said outer layer in a secured position with respect to each other.

12. A disposable diaper for an infant having a receiving space for infant solid waste to be stored away from the body comprising:
   an inner layer which is water pervious;
   an outer layer which is water impervious;
   an intermediate layer which has water retention capabilities;
   said inner layer having an opening shaped to surround a wearer's anal opening;
   said intermediate layer having a [cavity which is positioned at least partially under said opening of said inner layer] *cavity, larger than said opening, and positioned under said opening of said inner layer to entrap waste and preventing the waste from being spread over a substantial portion of a diaper;*
   means to hold said inner layer, said intermeidate layer and said outer layer in a secured position with respect to each other.

*14. A disposable diaper according to claim 1, said void being a cavity separating side segments of said intermediate layer, said disposable diaper further comprising means disposed about said side segments for restraining said cavity in an open condition.*

*15. A disposable diaper according to claim 14, said restraining means comprising a pair of ribbons passing through said cavity, one girting each of said side segments.*

*16. A disposable diaper according to claim 15, said cavity being an oval opening.*

*17. A disposable diaper according to claim 1, said outer layer having an oval opening therein and a pleat overlying an outer surface of said outer layer and confined to an area proximate said outer layer oval opening.*

*18. A disposable diaper according to claim 17, said pleat comprising an expansive fold integral with said outer layer.*

*19. A disposable diaper according to cliam 1, said void being a cavity separating side segments of said intermediate layer, said disposable diaper further comprising means disposed about said side segments for restraining said cavity in an open condition and said outer layer having an oval opening therein and a pleat overlying an outer surface of said outer layer and confined to an area proximate said outer layer oval opening.*

*20. A disposable diaper according to claim 19, said cavity and said outer layer oval opening at least partially overlapping.*

*21. A disposable diaper according to claim 20, said cavity being an oval opening substantially coincident with said outer layer oval opening.*

*22. A disposable diaper according to claim 20, said cavity separating side segments of said intermediate layer, said disposable diaper further comprising means disposed about said side segments for restraining said cavity in an open condition.*

*23. A disposable diaper according to claim 22, said restraining means comprising a pair of ribbons passing through said cavity, one girting each of said side segments.*

* * * * *